United States Patent [19]

Kwarteng

[11] Patent Number: 5,326,354
[45] Date of Patent: Jul. 5, 1994

[54] METHOD FOR FORMING ATTACHMENT SURFACES ON IMPLANTS

[75] Inventor: Kofi B. Kwarteng, New York, N.Y.

[73] Assignee: Howmedica Inc., New York, N.Y.

[21] Appl. No.: 87,360

[22] Filed: Jul. 2, 1993

Related U.S. Application Data

[63] Continuation of Ser. No. 891,669, May 29, 1992, abandoned, which is a continuation of Ser. No. 697,834, May 9, 1991, abandoned.

[51] Int. Cl.5 ............ A61F 2/54; A61F 2/32; B28B 11/08; B29C 33/76
[52] U.S. Cl. .................... 623/66; 623/901; 623/22; 264/293; 264/317
[58] Field of Search ............ 623/22, 66, 901; 264/293, 317

[56] References Cited

U.S. PATENT DOCUMENTS

| | | | |
|---|---|---|---|
| 3,893,196 | 7/1975 | Hochman | 62318/ |
| 4,054,701 | 10/1977 | Hahn | 264/293 |
| 4,058,701 | 10/1977 | Hahn | 264/293 |
| 4,568,505 | 2/1986 | Bollen et al. | 264/171 |
| 4,750,905 | 6/1988 | Koeneman et al. | 62316/ |
| 4,778,469 | 10/1988 | Lin et al. | 623/22 |
| 4,892,552 | 1/1990 | Ainsworth et al. | 623/23 |
| 4,902,297 | 2/1990 | Devanathan | 623/16 |

FOREIGN PATENT DOCUMENTS

| | | |
|---|---|---|
| 2350827 | 12/1977 | France . |
| 2182434 | 7/1990 | Japan . |
| 2183256 | 6/1987 | United Kingdom . |

Primary Examiner—Randall L. Green
Assistant Examiner—Debra S. Brittingham
Attorney, Agent, or Firm—Peter C. Richardson; Lawrence C. Akers; Raymond W. Augustin

[57] ABSTRACT

An improved method of producing a site for tissue ingrowth on a surgical implant by embedding a space occupier possessing a desired pattern in the surface of the implant at the desired location for ingrowth and then solubilizing the embedded space occupier to leave the pattern on the implant surface. Preferably, the implant is fabricated from a composite comprising a semi-crystalline thermoplastic resin such as polyetheretherketone or polyphenylene sulfide, and the space occupier is an acid-soluble metal plate machined to produce the desired pattern and removed by aqueous acid solution. The space occupier is embedded onto the composite surface by induction heating.

6 Claims, 3 Drawing Sheets

FIG-1
FIG-2
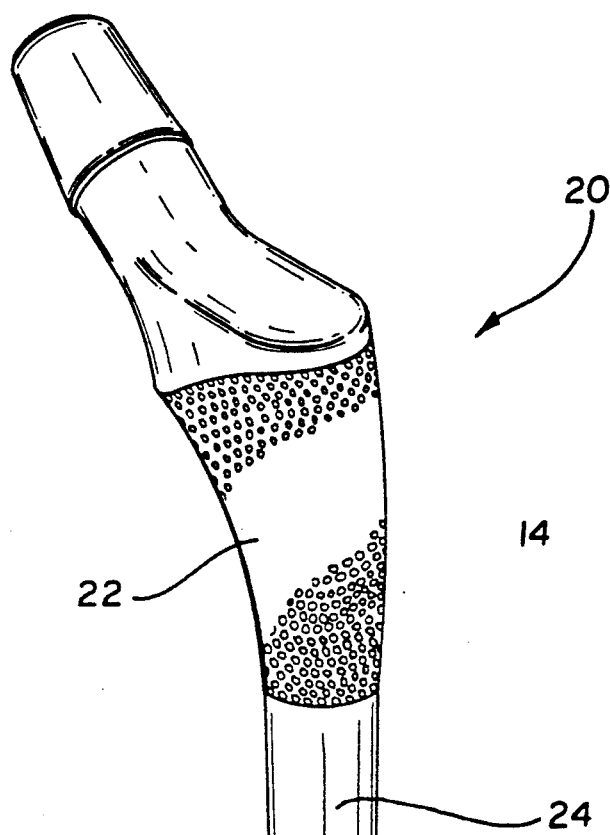
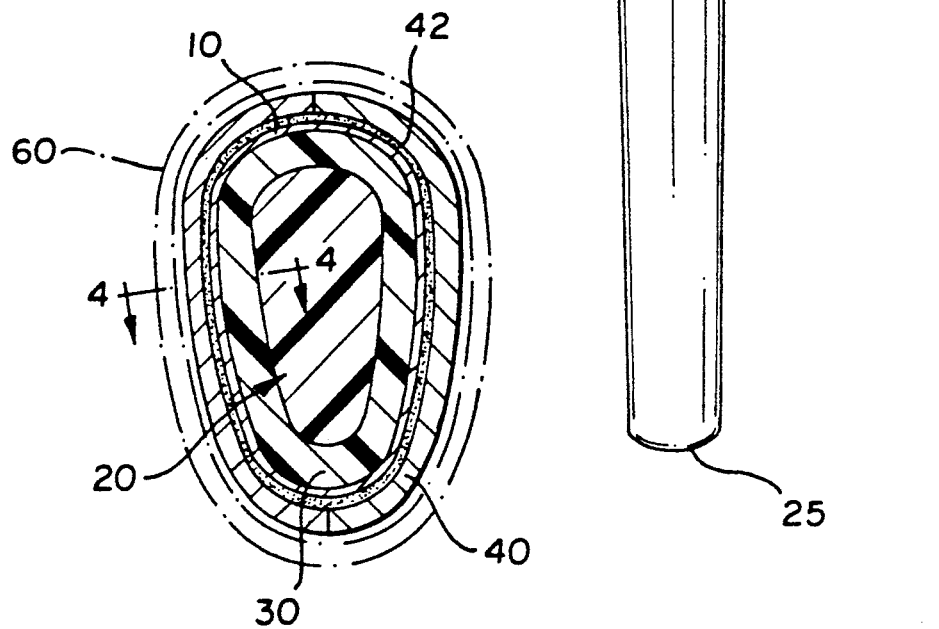

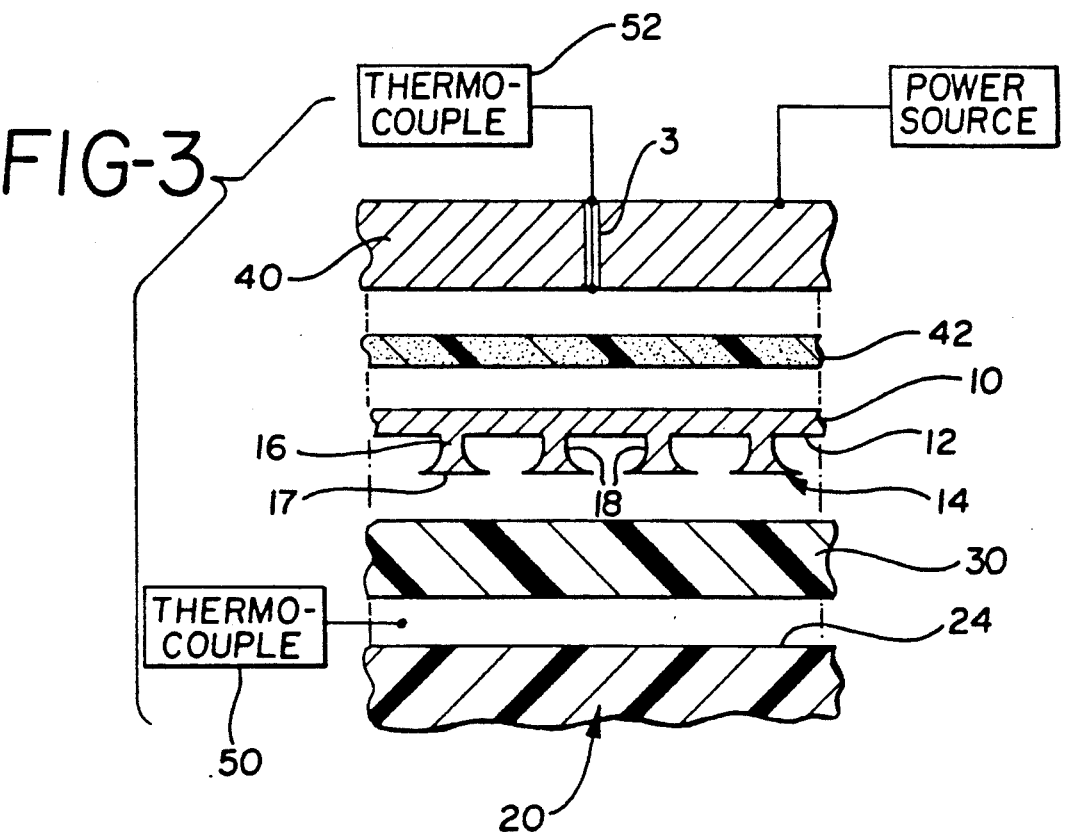
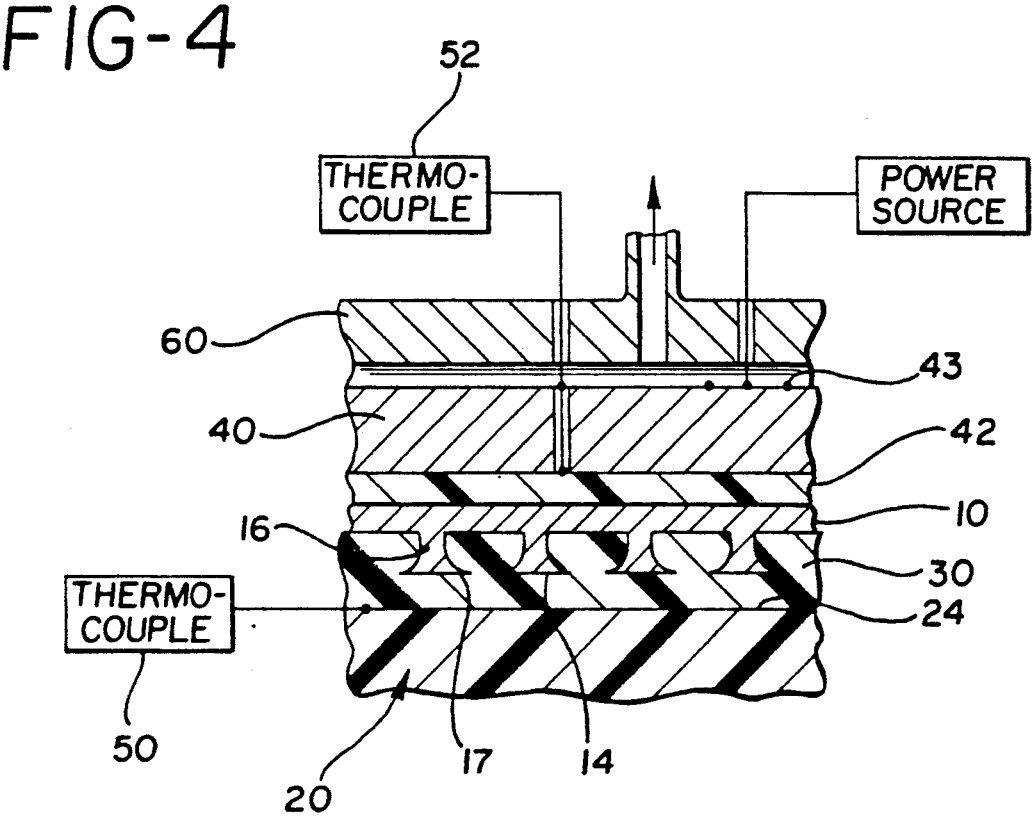

METHOD FOR FORMING ATTACHMENT SURFACES ON IMPLANTS

This is a continuation of application Ser. No. 07/891,669, filed on May 29, 1992 now abandoned, which is a continuation of application Ser. No. 07/697,834, filed on May 9, 1991, abandoned.

BACKGROUND OF THE INVENTION

1. Field of the Invention

This invention relates to a method of producing tissue ingrowth surfaces on surgical implants. More particularly, this invention relates to a method for forming attachment surfaces on implants made of composite materials.

2. Description of the Prior Art

Until recently, most surgical implants such as prosthetic hip stems were made of metal and implanted with the aid of bone cement to provide fixation of the implant in its desired location. With such fixation, however, the implant may tend to work loose from the cement, possibly causing failure of the implant or pain and discomfort to the patient. Alternative means of implant fixation have therefore been attempted.

Because metal implants are relatively stiff (having a high modulus of elasticity), the bone into which they are implanted is stressed in a manner different than under natural conditions. This causes the loss of bone tissue in areas which are not stressed, which bone loss can cause loosening. Therefore, lower modulus composite prostheses such as those described in U.S. Pat. Nos. 3,893,196, 4,750,905, 4,892,552 and 4,902,297 have been developed.

Since it is necessary to place the composite stem immediately adjacent the cortical bone surrounding the medullary canal, into which the implant is placed to insure proper stress transfer, bone cement cannot be used.

One alternative to cement fixation is the use of certain textures on selected areas of the implant surface to produce tissue ingrowth into these areas, and therefore stabilization of the implant. Several patterns for such texturized surfaces can be found in existing metal alloy prosthetic devices, or more recently, polymeric devices. However, the methods for forming fixation surfaces on polymeric devices have proved to be somewhat expensive. In addition, these methods tend to be slow and require exposure of the composite prosthesis to high pressure and temperature to form the ingrowth surface on the prosthesis. One such method is disclosed in U.S. Pat. No. 4,778,469, which while less expensive and lower in pressure and temperature than some other methods, has been improved upon in the present invention.

It is, therefore, the primary objective of the present invention to provide a simple and less expensive means for preparing desired texturized surfaces on body implants made from polymeric composites or other material systems.

SUMMARY OF THE INVENTION

The objective of the present invention is realized with the present method of producing tissue ingrowth sites on a surgical implant, which comprises the steps of embedding a space occupier possessing a desired pattern for tissue ingrowth on the surface of the implant at a selected portion of the implant where tissue ingrowth is desired by the use of induction heating, then solubilizing, the embedded space occupier with an agent nonreactive toward the implant to leave the desired pattern on the implant surface.

The space occupier is preferably in the form of an acid-soluble metal plate, suitably fabricated from magnesium, aluminum or zinc and machined to obtain the desired pattern, which is solubilized with an aqueous acid solution, or in the form of particulate water-soluble inorganic salt which is solubilized with water.

In the preferred embodiment, the space occupier is heated by induction heating and pressed into the implant surface, in which case the implant surface at the selected portion may be fabricated of a material which penetrates into undercuts in the space occupier more readily than that of the bulk of the implant, the material preferably being in the form of a sheet which fuses with the implant; the implant is fabricated from a composite comprising a thermoplastic resin, especially a semi-crystalline thermoplastic resin such as a polyetheretherketone or polyphenylene sulfide; and the implant is a joint prosthesis, especially a prosthetic hip stem.

The present invention also contemplates a surgical implant having a tissue ingrowth surface produced by the above method.

BRIEF DESCRIPTION OF THE DRAWINGS

In the drawings, wherein similar reference characters denote similar elements throughout the several views:

FIG. 1 is an isometric view of a composite hip implant having a proximal surface texture formed by the method of the present invention;

FIG. 2 is a cross-sectional view of the apparatus utilized to produce a surface texture according to the method of the present invention on a hip implant;

FIG. 3 is a partial cutaway view of the apparatus of FIG. 2 along lines 3—3;

FIG. 4 is the apparatus of FIG. 3 after completion of the molding process;

DETAILED DESCRIPTION OF THE INVENTION

The method of the present invention provides a simple and economical means for producing complex texturized fixation patterns on surgical implants, made of polymeric composites or other material systems, in a controlled and reproducible manner, such patterns often being impossible to produce by existing techniques. Existing techniques of compression molding allow for a two surface pattern (namely medial and lateral), only while the present technique makes circumferential coverage possible. In addition, heating done locally avoids the need to heat the entire structure, which heating tends to disrupt fiber pattern in the substrate. It is also quicker than molding the entire substrate.

The desired fixation pattern on the implant is readily established by the shaping or machining of the removable space occupier, and since the pattern is created in the implant material itself, the potential problem of weakening at the boundary of the fixation phase and the implant material encountered with certain present methods, such as those for prostheses having sintered metal implant surfaces, does not exist.

Such a fixation pattern is shown in FIGS. 3-6 of the drawings. Here the space occupier is a machined or photo-etched, acid-soluble plate 10, fabricated from metals such as aluminum, magnesium or zinc. By space occupier is meant a substance nonreactive with the material of construction of a surgical implant and possessing a pattern which is to form the surface pattern on a limited area desired to be transferred to a selected surface of the implant by embedding the substance with its pattern in that surface and then solubilizing the substance with an agent which does not react with the implant, thereby leaving the desired pattern on the surface of the implant.

Figure 6:
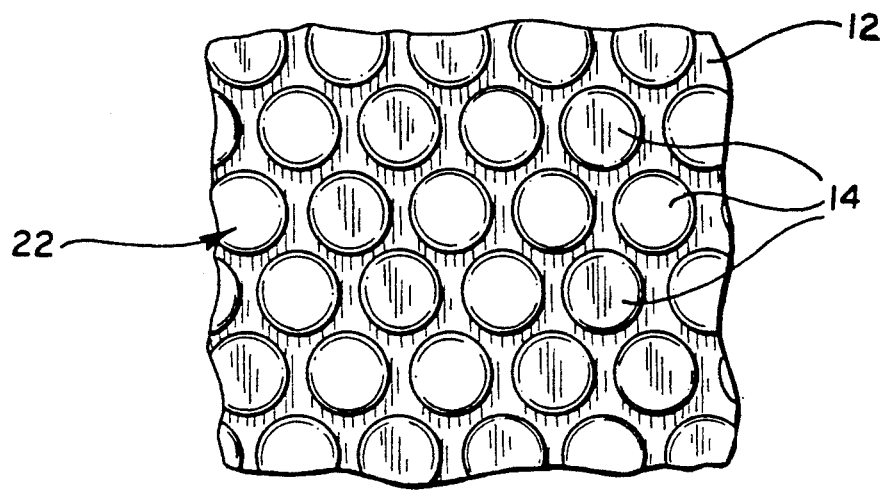
FIG. 6 is a plan view of the surface texture of FIG. 5.

The preferred plate 10 has a surface 12 with the repeat pattern 14 shown in FIG. 6. Preferred pattern 14 includes tapered posts 16 forming undercuts 18 with a circular top 17 as shown in FIGS. 3 and 4. Plate 10 may be fabricated of any material in which the desired pattern for the texturized surface of an implant may be formed and with which the implant is compatible or nonreactive. Likewise, the solubilizing agent for the plate may be any substance which will solubilize and remove the plate without reacting with or otherwise affecting the implant to thereby leave the transferred pattern intact in the implant surface. For example, when the implant is fabricated from such semicrystalline thermoplastic polymers as polyetheretherketone (PEEK) or polyphenylene sulfide (PPS), with or without carbon fiber reinforcement, the plate may be fabricated from a metal such as aluminum or magnesium and solubilized with aqueous hydrochloric acid or sodium hydroxide; zinc and solubilized with aqueous hydrochloric acid; or silver and solubilized with aqueous nitric acid.

Figure 5:
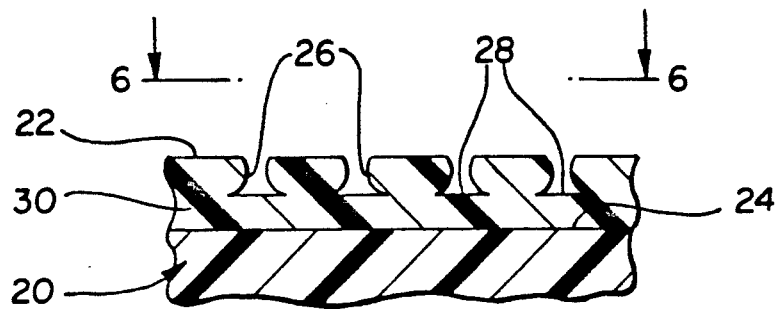
FIG. 5 is a partial cross-sectional view of the surface texture produced by the method of the present invention.

When pattern 14 is to be transferred to a body implant, such as the prosthetic hip stem 20 shown in FIG. 1, a plate 10 of FIG. 2 is cut or formed to a desired shape and size, such as area 22, and then embedded in the surface 24 of stem 20. If stem 20 is fabricated from a thermoplastic resin such as PEEK or PPS, plate 10' may be pressed into stem 20 by induction heating at a temperature at or above the softening point of the resin. Embedded plate 10 is then solubilized with a solubilizing agent such as dilute aqueous hydrochloric acid to leave a texturized surface on stem 20 having a profile as shown in FIG. 5. Now the undercuts 18 of tapered post 16 of plate 10 have become undercuts 26 of stem 20, while circular top 17 of plate 10 has become base 28 of surface 24 of stem 20.

In a preferred embodiment of the present method, as shown in cutaway in FIGS. 3 and 4, intermediate sheet 30 is placed between plate 10 and surface 24 in area 22 prior to embedding plate 10. Sheet 30 is fabricated of a material which fuses to surface 24 and penetrates into undercuts 18 of pattern 14 more readily than the material of surface 24 and the bulk of stem 20. This insures that undercuts 26 and surface 28 of the texturized surface on area 22 are well defined, and at the same time avoids a discontinuity between the fixation surface and the bulk of stem 20. Thus, for example, implant 20 may be fabricated of a PEEK prepreg containing 60 weight percent unidirectional carbon fibers to provide a strong stem prosthesis, while sheet 30 may be fabricated from PEEK containing up to 30 weight percent chopped carbon fiber pellets to insure a well defined tissue in-growth area 22 on the prosthesis which is integral with stem 20. The use of sheet 30 may be incorporated on plate 10 prior to placing it over the prosthesis 20 or may be done in the same heating step in which the plate 10 sheet 30 is molded onto prosthesis 20.

The implant material itself need only be capable of being embedded by the space occupier and inert to both the space occupier 10 and the solubilizing agent 30. Thus, in addition to the semi-crystalline thermoplastic resins mentioned above, the implant material, for example, may be other thermoplastic resins such as polyethylene and polypropylene; thermosetting resins such as epoxy and phenolformaldehydes; ceramics such as hydroxyapatite; pyrolytic carbon; and metals such as Vitallium ® or titanium. Those skilled in the art will be able to select the proper combination of implant material, space occupier and solubilizing agent.

As shown in FIG. 2, sheet 30 and plate 10 may be formed as a sheet and then wrapped around the proximal area 22 of stem 20. Alternately, sheet 30 and plate 10 may be preformed with a shape capable of sliding over tip 25 of stem 20 and up to area 22 thereon.

An outer metal plate or susceptor 40 surrounds metal plate 10' so that plate 10 may be heated via induction heating. A release film 42 is utilized so that susceptor 42 may be easily disengaged from plate 10. The preferred release film 42 is a Kapton ® (a polyamide) film 0.020" thick which may be obtained from DUPONT.

The induction heat results from the electrical current induced in susceptor 40 which is magnetically connected to a primary metal, such as wires 43, carrying electrical current. The induction bonding consists of a power source that causes current and heat to be generated in a secondary element such as a susceptor. The susceptor 40 heats plate 10 by conduction.

In the preferred method, susceptor 40 was used and was formed so that with the PEEK-impregnated magnesium, the PEEK adhesive, and Kapton ® film 42 correctly positioned around the hip, a snug fit would be achieved when the hip was inserted into the susceptor 40. Susceptor 40 includes a clamping device (not shown) to assure that the proper fit between hip, hip materials, and susceptor 40 was maintained during the bonding operation.

A heating head (not shown) consisting of four 3" diameter, ¼" wide toroid cores was gapped so that the total stainless steel susceptor 40 could be inserted inside the machined gap. Nine turns of five-conductor #18 gauge copper wire were wound around the cores forming an induction heating device that produced sufficient heat to heat the hip susceptor or mold 40° to 720° F. in approximately three minutes.

The preferred method for forming a surface texture on a hip stem 20 uses a 0.8 mm thick sheet 30 prepared by compression molding a composite mixture of 30 weight percent chopped carbon fiber pellets (CCF)[(1)] in a polyetheretherketone (PEEK) matrix or, alternatively PEEK film which may be obtained commercially. Sheet 30 is placed between a magnesium plate 10 having on its lower surface the premachined pattern as shown in FIGS. 3-6 and composite hip stem 20 made of 60 weight percent carbon fibers (CF) in PEEK[(2)] with a thermocouple 50 placed between sheet 30 and surface 24 of stem 20 at the edge. The impregnation of plate 10 with sheet 30 may also be performed prior to placing plate 10 on the substrate, i.e. surface 24 of stem 20.

(1) 450CA30 pellets, ICI, Wilmington, Del.
(2) APC-2 prepreg, ICI

Kapton ® release film 42 is placed on top of the PEEK infiltrated magnesium plate and susceptor 40 is then placed on top of the release film.

The induction heating head is then connected to a power supply (T-4000 Torobonder, Inductron Corp., Grafton, Va.). The entire arrangement is placed in a metal mold or susceptor 40 fabricated to circumferentially enclose the proximal section 22 of stem 20 and fitted with clamps and a port through which thermocouple 52 is inserted to record the outside temperature. Preferably, the entire assembly is placed under a vacuum system 60.

The exterior surface of mold 40 is then clamped shut and inductively heated (150 W power) at 35% level with the following temperature profile recorded at the outside and at the bond line (between sheet 30 and stem 20):

| TIME (min.) | TEMPERATURE (°F.) | |
|---|---|---|
| | OUTSIDE Thermocouple 52 | BONDLINE Thermocouple 50 |
| 1 | 250 | 258 |
| 2 | 360 | 337 |
| 3 | 425 | 435 |
| 4 | 480 | 515 |
| 5 | 615 | 600 |
| 6 | 720 | 660 |
| 7 | 725 | 700 |

When the bond line temperature recorded by the thermocouple 50 reaches about 720° F., usually between 700° and 750° F., the induction heating is discontinued. The system is disassembled after air-cooling. A bond between the PEEK infiltrated magnesium plate and the APC-2 substrate results with the intervening PEEK film, and the resin phase of the substrate and magnesium all fuse into a visually indistinguishable mass.

The outside surface of the magnesium side (top) is then sanded lightly to remove the PEEK polymer from the surface. The exposed metallic surface was then placed in an acid medium according to the method of U.S. Pat. No. 4,778,469 and yielded a textured APC-2 panel.

Specifically, the implant is dipped into a 3M aqueous hydrochloric acid solution to solubilize the magnesium plate, leaving a composite implant with a textured surface having a clean, orderly pattern the inverse of that of the original magnesium plate.

Figure 7:
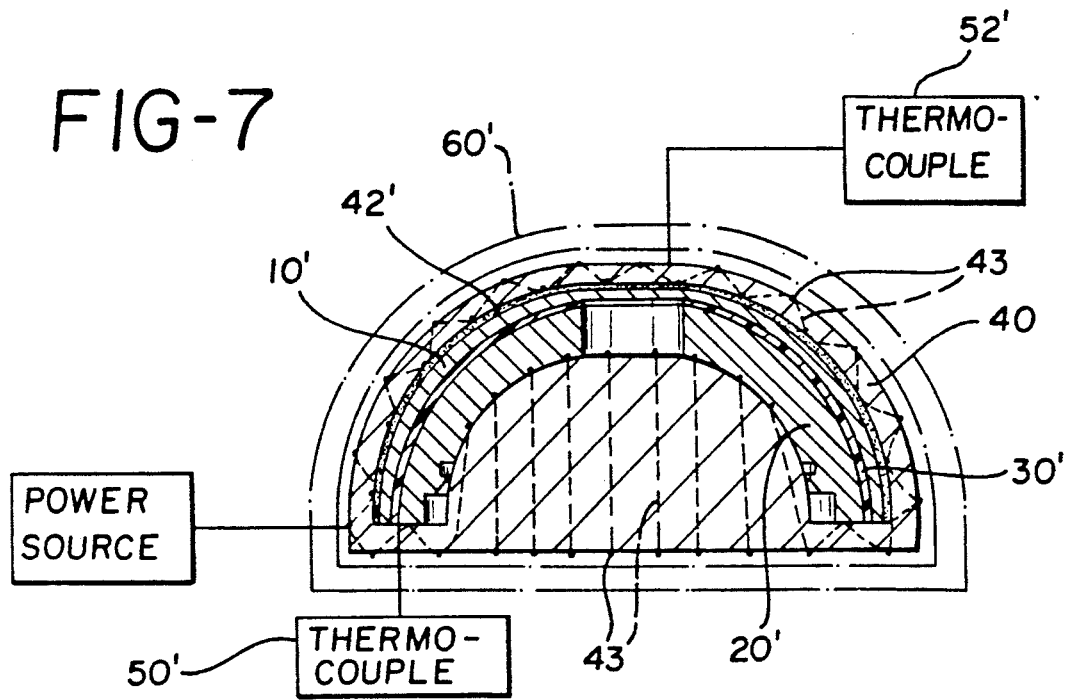
FIG. 7 is a cross-sectional view of an apparatus utilized to produce a surface texture according to the method of the present invention on an acetabular cup.

Referring to FIG. 7 there is shown an apparatus almost identical to that described above, but for use in forming a surface texture on composite acetabular cup 20'. The composite cup 20' is covered by a sheet 30' similar to sheet 30 described above. A metal texture plate 10' covers sheet 30' and is in turn covered by Kapton ® release film 42'. A metal susceptor plate 40' is used for induction heating plate 10'. Again, thermocouples are used to monitor temperature during the heating process, which is the same as that described above.

While the above description and examples have been directed primarily to a hip stem or acetabular cup prosthesis, the method of the present invention may also be employed with other prosthetic devices, as well as with other surgical implants, including cardiovascular implants, ligaments and tendons, which profit from a tissue ingrowth surface.

I claim:

1. A method of producing a site for tissue ingrowth on at least a portion of a surface of a compression molded composite surgical implant comprising the steps of:

placing a metal space occupier possessing a desired tissue ingrowth pattern over the portion of the surface of the molded composite surgical implant;

placing a release film over the space occupier;

placing a tightly fitting metal susceptor over the release film in the area of said space occupier;

clamping said susceptor over said implant in a fixed position with respect thereto with a clamp;

heating only the surface of said composite implant by heating said metal space occupier by induction heating to a temperature above a melting point of the composite implant in the presence of only a thermal expansion force generated by said heating with said clamp in place to allow the space occupier to become embedded therein; and solubilizing the embedded space occupier with an agent non-reactive toward the implant to remove the space occupier and leave the desired pattern in the implant surface to accept tissue ingrowth.

2. The method as set forth in claim 1 wherein said temperature is between 700° and 750° F.

3. The method as set forth in claim 1 wherein the release film is made of a polyamide.

4. The method as set forth in claim 1 wherein the implant is formed from a semicrystalline thermoplastic.

5. The method as set forth in claim 4 further including the step of placing a sheet of a second semicrystalline thermoplastic material capable of bonding to the composite implant, but having flow properties better able to penetrate into the ingrowth pattern of said space occupier than said thermoplastic, between said implant and said space occupier.

6. A method of producing a site for tissue ingrowth on a compression molded composite surgical implant, said implant having curved surfaces, comprising the steps of:

placing a metal space occupier possessing a desired tissue ingrowth pattern over at least a portion of the curved surfaces of the composite surgical implant;

placing a release film over the space occupier;

placing a tightly fitting metal susceptor over the release film in the area of said space occupier;

clamping said susceptor over said implant in a fixed position with respect thereto with a clamp;

heating only the surface of said composite implant by heating said metal space occupier to a temperature above a melting point of the composite implant in the presence of only a thermal expansion force generated by said heating with said clamp in place to allow the space occupier to become embedded therein; and solubilizing the embedded space occupier with an agent non-reactive toward the implant to remove the space occupier and leave the desired pattern in the implant surface to accept tissue ingrowth.

* * * * *